US 6,740,063 B2

United States Patent
Lynn

(10) Patent No.: US 6,740,063 B2
(45) Date of Patent: May 25, 2004

(54) LUER RECEIVING VASCULAR ACCESS SYSTEM

(76) Inventor: Lawrence A. Lynn, 362 Curleys Ct., Worthington, OH (US) 43235

( * ) Notice: Subject to any disclaimer, the term of this patent is extended or adjusted under 35 U.S.C. 154(b) by 0 days.

(21) Appl. No.: 10/270,129

(22) Filed: Oct. 15, 2002

(65) Prior Publication Data

US 2003/0040724 A1 Feb. 27, 2003

Related U.S. Application Data

(63) Continuation of application No. 09/636,761, filed on Aug. 14, 2000, now Pat. No. 6,485,473.
(60) Provisional application No. 60/148,346, filed on Aug. 12, 1999.

(51) Int. Cl.[7] ............................................... A61M 5/00
(52) U.S. Cl. .................................. 604/256; 604/167.03
(58) Field of Search ........................... 62/256, 122, 126, 62/167.01, 167.02, 167.03, 168.01, 900, 905, 246, 248, 249, 250

(56) References Cited

U.S. PATENT DOCUMENTS

| 4,314,555 A | 2/1982 | Sagae |
| 4,496,348 A | 1/1985 | Genese et al. |
| 4,512,766 A | 4/1985 | Vailancourt ............. 604/256 X |
| 4,758,225 A | 7/1988 | Cox et al. .................... 604/126 |
| 4,935,010 A | 6/1990 | Cox et al. .................... 604/122 |
| 5,085,645 A | 2/1992 | Purdy et al. |
| 5,211,634 A | 5/1993 | Vaillancourt |
| 5,221,634 A * | 6/1993 | Cho et al. |
| 5,295,969 A | 3/1994 | Fischell et al. ............. 604/168 |
| 5,395,342 A * | 3/1995 | Yoon ....................... 604/167.03 |
| 5,409,461 A | 4/1995 | Steinman |
| 5,429,616 A | 7/1995 | Schaffer |
| 5,447,501 A | 9/1995 | Karlsson ..................... 604/198 |
| 5,498,247 A | 3/1996 | Brimhall |
| 5,531,810 A | 7/1996 | Fullenmann |
| 5,542,933 A * | 8/1996 | Marks ..................... 604/249 X |
| 5,556,387 A | 9/1996 | Mollenauer et al. |
| 5,575,777 A | 11/1996 | Cover et al. ................. 604/197 |
| 5,749,859 A | 5/1998 | Powell |
| 5,911,705 A | 6/1999 | Howell ......................... 604/110 |
| 5,951,515 A | 9/1999 | Osterlind .................... 604/110 |
| 5,967,490 A | 10/1999 | Pike |
| 6,077,244 A | 6/2000 | Botich et al. ................ 604/110 |
| 6,171,287 B1 | 1/2001 | Lynn et al. .................. 604/256 |
| 6,217,556 B1 * | 4/2001 | Ellingson et al. ......... 604/256 X |
| 6,228,060 B1 | 5/2001 | Howell |
| 6,344,033 B1 | 2/2002 | Jepson et al. |

FOREIGN PATENT DOCUMENTS

| WO | WO 96/23158 | 8/1996 |
| WO | WO 98/23313 | 6/1998 |

\* cited by examiner

*Primary Examiner*—Harry B. Tanner
(74) *Attorney, Agent, or Firm*—Nixon & Vanderhye PC

(57) ABSTRACT

A catheter system for fluid connection between a patient's vasculature and a fluid system that has a luer lock connector including a luer tip. The catheter system includes a catheter having a hub having an open end sealed with an elastomeric septum. The hub defines a female luer sized to be received into and locked to the connector of the fluid system when the luer tip is advanced into the septum. A needle extends through at least a portion of the septum, the needle having a tip projecting adjacent the catheter tip and a needle hub disposed adjacent the outer face of the septum. The needle is removable from the catheter and septum after the catheter is advanced into a blood vessel. The elastomeric septum seals subsequent to withdrawal of the hollow needle to provide a sealed outer face for engaging and receiving the luer tip.

52 Claims, 5 Drawing Sheets

LUER RECEIVING VASCULAR ACCESS SYSTEM

This application is a continuation of application Ser. No. 09/636,761 filed Aug. 14, 2000, U.S. Pat. No. 6,485,473 the disclosure of which is incorporated herein by this reference. This application also claims the benefit of U.S. Provisional Application Serial No. 60/148,346, which was filed Aug. 12, 1999, the disclosure of which is incorporated herein by this reference.

BACKGROUND AND SUMMARY OF THE INVENTION

The risk of needle stick during the insertion of a peripheral catheter into a patient is well known. Such catheters generally utilize an internal needle which projects beyond the tip of the catheter for insertion into a vein. A variety of safety devices have been developed which retract the needle from the catheter into an enclosed container, thereby preventing needle stick after the catheter has been inserted. However, such catheters after insertion can still pose a risk of blood exposure to the nurse inserting the device because the end of the catheter is open or will need to be opened if luer access is desired so that blood can drip from the hub of the catheter after the catheter has been inserted and the needle has been withdrawn. This represents a serious problem and requires meticulous technique to prevent significant blood exposure. Nurses often try to occlude the vein adjacent the tip of the catheter so as to prevent blood from refluxing back into the catheter and out the hub during the engagement of a luer fitting to the catheter. The open hub is generally attached to a heparin well (also called a saline well or prn adapter). Alternatively, an IV tubing may be connected directly to the catheter hub. In both these situations the connection needs to be made quickly to keep blood from refluxing out the open hub. Another technique is to hold the finger or thumb over the tip of the hub while preparing the heparin well for attachment to the hub.

Another problem is that direct luer access to a patient's vascular system generally requires the attachment of a secondary device, such as a heparin well, which comprises a chamber connected to a luer receiving valve. These secondary devices are expensive and cumbersome to attach when blood is leaking out the hub. Indeed blood, leaking out of the hub often is caught in the threads of the saline well where it forms a potential source for bacterial colonization. In addition, such heparin wells can become disconnected, exposing the patient's vascular system to the introduction of air or microorganisms and can result in silent death due to bleeding out the hub when the disconnection is unnoticed as during sleep.

U.S. Pat. No. 4,758,255 to Cox et. al. discloses a catheter having a closed hub. This patent provides background for the present invention. However, this device of Cox requires an adapter to mate with a luer connector eliminating the desired self-sealing function. Further, no mechanism to mitigate the negative pressure associated with luer withdrawal is provided and there is no needle protection mechanism.

The present invention comprises a closed luer vascular access system, which can allow for the safe withdrawal of the needle from the catheter hub while still preventing reflux of blood out the hub before and during any future luer access of the hub after the catheter has been inserted.

The present invention comprises a catheter having a hub. The hub includes a luer-receiving valve, which can be for example of the types described in my U.S. Pat. No. 6,171,287, the entire disclosure of which is incorporated by reference as if completely disclosed herein. The closed luer access system further includes a needle sized and configured to project through the luer-receiving valve and into the lumen of the catheter so that the sharp point of the needle projects beyond the tip of the catheter. The needle preferable includes the hub, which projects proximally away from the face of the luer receiving valve. The hub preferably includes a lumen, which is enclosed and vented to the atmosphere so that blood can reflux through the needle and into the hub when the catheter containing the needle is inserted into the vein.

The luer-receiving valve, which is interposed between the catheter and the needle hub, preferably, surrounds and is attached to the proximal end of the projecting plastic catheter thereby comprising the hub of the projecting catheter. The one preferred embodiment includes the plastic catheter defining a distal end and a proximal end and a lumen there through. The proximal end of the catheter is connected with a hub. The hub includes a lumen and a proximal end and an elastomeric sealing member occluding the proximal end. The sealing member has a perforation sized and configured to receive a luer male end. The hub and the elastomeric sealing member are sized and configured to be received within a luer lock end of a conventional IV connection terminal or syringe. The closed luer access system further includes a needle having a sharp distal end and a proximal end and a hub connected to the proximal end. The needle defines a lumen extending from the sharp distal end to the hub. The hub defines a lumen which is preferably vented to the outside atmosphere so that blood which enters the lumen of the needle through the tip upon insertion of the needle into the vein can reflux through the needle into the hub so that entry into the vein can be identified by the nurse through the visualization of the blood refluxing back into the lumen of the needle hub. In one preferred embodiment the needle hub includes an open proximal end and a filter which is permeable to air but not to blood occluding the open proximal end. In a presently preferred embodiment, the closed luer access system further includes a retractor for retracting the needle out of the catheter and out of the luer receiving valve hub after the catheter has been inserted into the vein. The retractor can include a spring, which can be held in a compressed state prior to the insertion of the catheter and then released by a trigger to engage the needle hub and thereby retract the needle hub out of the catheter. In operation, the nurse preps the patient's skin and inserts the catheter into the vein. Once the reflux of blood is identified within the needle hub the nurse advances the catheter over the needle into the vein and once he or she is sure that he catheter is in adequate position the trigger is pressed which releases a spring so that it expands and pulls the needle out of the catheter and out of the luer receiving valve catheter hub and into a receptacle wherein it is safely contained. At this point, the enclosed catheter is immediately ready for use and for closed luer access and there is no need for the attachment of a heparin well, saline well or other luer access based catheter-closing device.

It is the purpose of the present invention to provide a closed luer access system which includes an integral luer receiving valve hub configured to mitigate the negative pressure associated with withdrawal of the luer tip from the valve so that the attachment of a saline well is no longer required.

It is further the purpose of the present invention to provide a closed luer access system having a luer receiving valve hub and a retractor for retracting the needle throughout the luer receiving valve hub out of the closed luer access system.

It is further the purpose of the present invention to provide a closed luer access system having a luer receiving valve hub connected to a needle-receiving receptacle so that the needle can be retracted from the catheter into the needle-receiving receptacle.

It is further the purpose of the present invention to provide an automatic retractor such as a spring adjacent the needle so that the needle can be automatically retracted out of the luer receiving valve hub.

It is further the purpose of the invention to provide a catheter having an integral luer receiving valve hub so that upon inadvertent disconnection of the catheter from an attached IV tubing system does not result in an open passageway from the environment into the patient's vascular system.

It is further the purpose of the invention to provide a catheter having an integral luer receiving valve hub with a flexible tube intermediate the catheter and the valve hub to allow the luer to be threaded onto the hub without transferring torsion force to the catheter and vein.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which.

DESCRIPTION OF THE PRESENTLY PREFERRED EMBODIMENT

Figure 1:
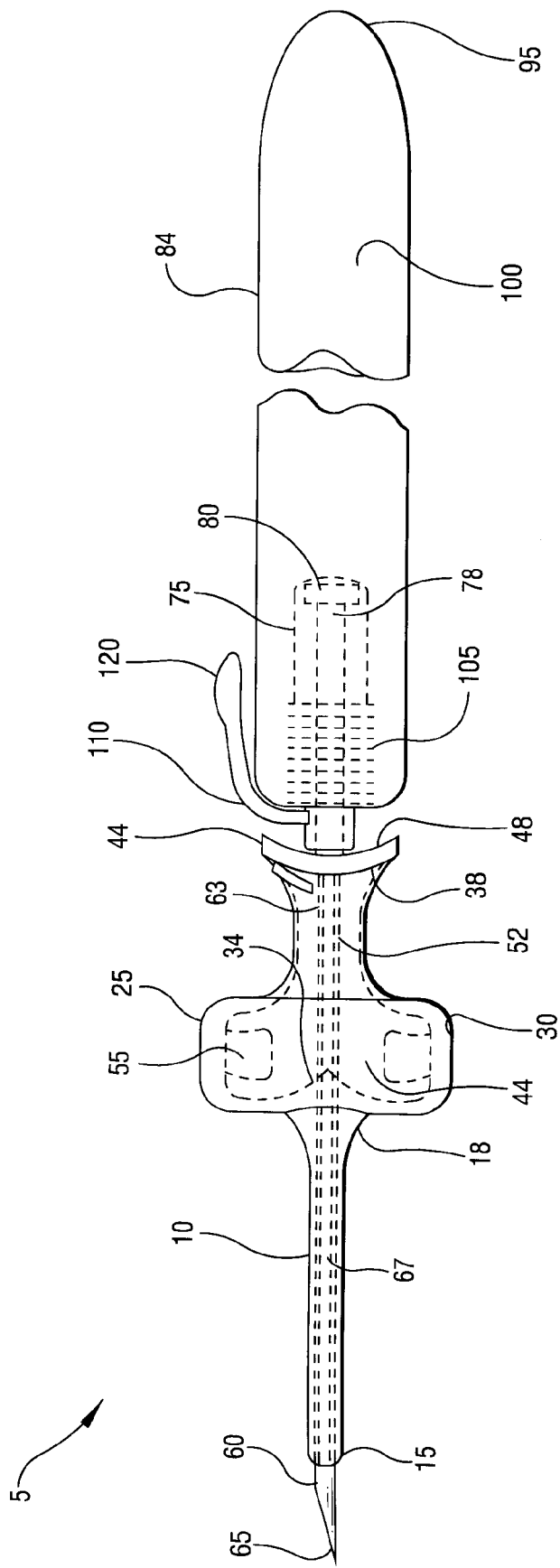
FIG. 1 is a perspective view of the closed luer access system according to the present invention.

The closed luer receiving vascular access system 5 includes a flexible tubular catheter 10 having a tapered distal end 15 and a proximal end 18 and an internal lumen 20. A luer receiving valve hub 25 is connected to the proximal end 18 of the catheter 10 and includes the housing 30 and defining an internal chamber 34 and a proximal end 38. As shown, the chamber 34 is preferably of small volume, thereby minimizing any trapped air so that the system 5 is immediately available for use minimizing the need for aspiration of air from the system 5. (However the closed aspiration of deadspace air through the system 5 is easily accomplished prior to flushing using any conventional luer lock syringe.) An elastomeric sealing member 44 is provided sealing the proximal end 38 of the housing 30. The elastomeric sealing member 44 defines an outer face 48 and includes a slit 52 extending from the outer face 48 to the chamber 34. Both the proximal end 38 of the housing 30 and the slit 52 are sized and configured to be received within a standard luer lock end as described in the aforementioned '287 patent. Cavities 55 are provided to receive lateral deflection of sealing member 44 away from chamber 34. It is preferable that the luer receiving valve hub 25 have features to mitigate the negative pressure induced within the fluid chamber 34 upon luer tip withdrawal or to induce positive pressure within the fluid chamber upon withdrawal. These features are described in detail in the aforementioned '287 patent and can include the provision of sealing member 44 having a length nearly equal to or greater than the length of the projecting luer tip. Also, the provision of lateral cavities 55 to provide for lateral deflection away from the fluid chamber 34 is another means to mitigate such negative pressure. To minimize penetration force these cavities 55 can be very large, if desired. This allows luer access into the closed space adjacent the catheter without reflux of blood with the catheter tip upon luer withdrawal.

A needle 60 is provided having a sharp distal tip 65 and a needle lumen 67 extending to a needle hub 75, having a hub lumen 78 extending to a proximal end 80. During assembly, the needle 60 can be inserted through the slit 52 or can be inserted at a position lateral to the slit 52 so that the slit 52 is not separated by the needle 60. The needle hub 75 is contained within a needle receptacle 84, which includes an enclosed proximal end 95 and defines a receptacle chamber 100 for receiving the retracted needle as will be discussed. The receptacle 84 further contains a retraction spring 105 positioned adjacent the needle hub 75. The retraction spring 105 is held in its compressed position by a trigger retainer 110. The trigger retainer 110 includes a button 120 facing outwardly and the retainer 110 is e.g. selectively radially engaged with a portion of hub 75 such that finger pressure against the button 120 causes the retainer 110 to shift in position, releasing the hub 75 from its retained position thereby allowing the spring 105 to actively retract the needle 60 back into the receptacle chamber 100. The receptacle retainer and spring mechanism can be of the type marketed under the name "Autoguard" by Becton Dickinson.

In operation, the luer receiving vascular access system 5 is packaged with the needle 60 fully advanced through the luer receiving valve hub 25 and the catheter 10 such that the sharp needle tip 65 projects slightly beyond the distal tapered end 15 of the catheter 10. The spring 105 is in the compressed position with the needle hub 75 held in its forward advance position by the retainer 110. After the nurse has prepped the skin he or she advances the needle 60 with its associated catheter 10 into the vein and then observes the "flashback" of blood at the needle hub 75. At this point, the plastic catheter 10 is advanced off the needle 60 deeper into the vein by pushing gently on the luer receiving valve hub 25. Once the position of the catheter 10 is assured within the vein the button 120 is pressed releasing the needle hub 75 so that the spring 105 actively pulls the needle hub 75 and its associated needle 60 out of the catheter 10 through the luer receiving valve hub 25 and into the needle receptacle 84. With this system there is no need for occluding the vein upstream since back flow cannot occur and direct luer access is immediately assured.

At this point, the task is completed. The catheter is now positioned within the vein as a completely enclosed direct luer vascular access system ready to receive a luer end such as the syringe or an IV tubing system. The system therefore allows immediate luer access to the blood vessel of the patient for infusion of medication or blood collection utilizing a blood collector having a luer tip as are known in the art.

Figure 2:
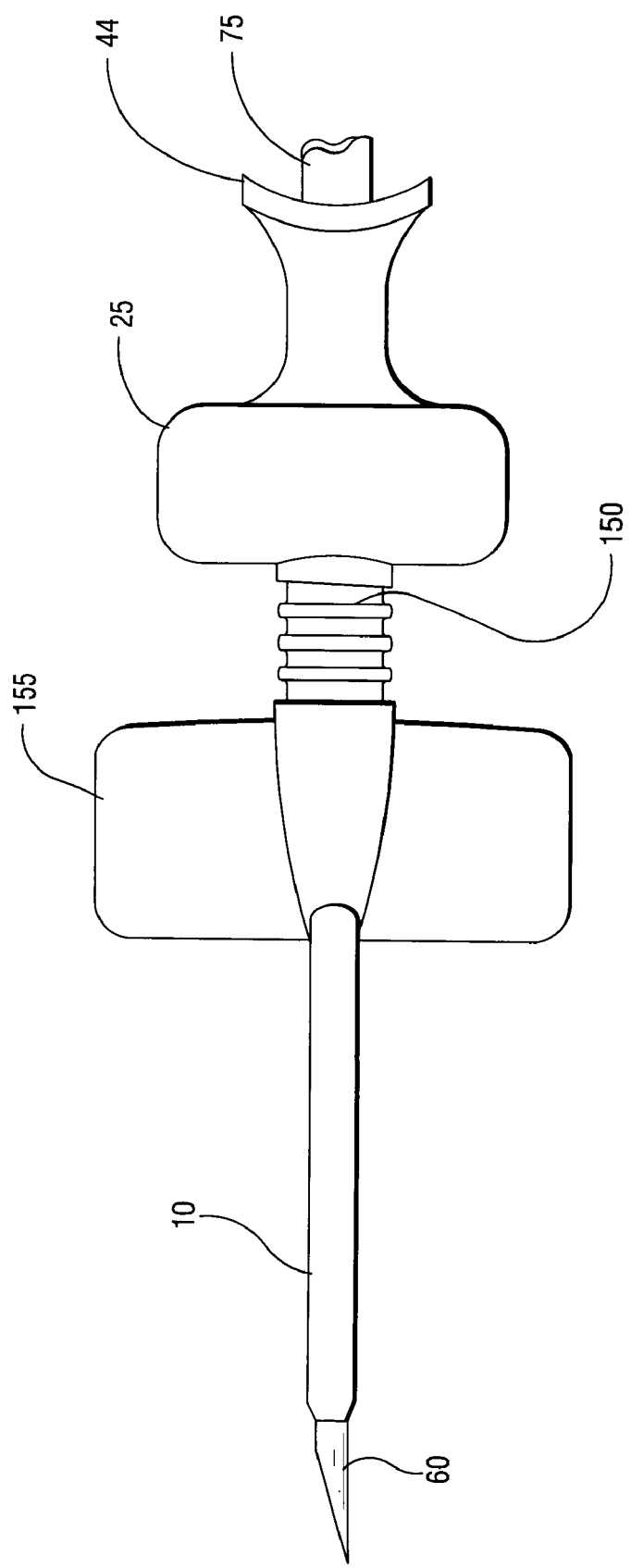
FIG. 2 is a perspective view of the closed luer access system of FIG. 1 with a modification providing a highly flexible tube intermediate the catheter and luer hub.

FIG. 2 shows the vascular access system shown in FIG. 1 modified to limit stress on the vein. The attachment of a luer connector to the closed luer receiving valve hub 25 provides a new challenge of avoiding the transmission to catheter 10 the forward forces associated with penetration in the valve combined with the simultaneous torsional connecting forces associated with threading onto the valve. These connecting forces are generally greater than those associated with a conventional needle connection or attachment to conventional open hub. It is also important to minimize the transmission of flexion forces which can be associated with the elevation of the valve hub 25 during attachment of a conventional threaded luer connector while the catheter 10 is within a delicate vein. For this purpose there is provided a flexible tube 150 intermediate the catheter 10 and the luer receiving valve hub 25. The tube 150 can be comprised of soft silicone for example, and preferably includes integral tape-down wings 155. The tube 150 can include a hinge to minimize the risk of kinking while enhancing the flexibility so that the hub 25 can be held and elevated with one hand to hold the hub 25 securely during attachment to thereby minimizing the transmission or torsion or other stress from the hub 25 to the catheter 10. It is preferable for the tube 150 to be sized and configured intermediate the proximal end 18 and the luer receiving valve hub 25 to allow a high degree of flexion along the tube 150 so that elevation can be easily achieved for valve hub 25 attachment and disconnection but it is also preferable to accomplish this with minimal addition of length intermediate the catheter 10 and valve hub 25 so that the length of the needle is minimized. In the presently preferred embodiment of FIG. 2 the tube 150 can be 8 mm–20 mm in length although other lengths can be used. If preferred the tube 150 can be deeply pleated at multiple levels along is length (not shown) to provide greater flexibility. Such a pleated tube can be mounted in a compressed or longitudinally folded configuration (for example, with each pleat intussuscepted into the adjacent pleat to provide a greater operational length but a smaller resting length to limit the need for a longer internal needle 60 through the tube 150. If preferred, a removable cylindrical outer rigidity stent (not shown) can be provided in place over the flexible tube 150 during the insertion process to assure optimal initial alignment.

If preferred, to allow use of a very long integral flexible extension tube (as for example ten centimeters) mounted immediate the catheter and the luer receiving valve hub, the needle can be shorter and the proximal end of the needle connected to a flexible-retracting member (the use of short needles connected to needle-retracting members is well known in the art) such as a wire or fine tube. The flexible member can extend from the needle through the flexible extension tube and then through luer receiving valve hub where it can be grasped after the catheter has been inserted into the vein to allow the needle to be pulled through a flexible the valve hub. The use of a flexible needle-retracting member allows the luer receiving valve hub to be positioned at the proximal end of an integral extension tube remote from the catheter hub while still providing for the aforementioned advantages of the invention.

When a larger bore catheter 10 is used (such as those greater than 20 gauge) the needle 60 will need to have a complimentary larger diameter adjacent the catheter tip 15. If this diameter is extended to the proximal segment of the needle 63, this can increase the internal displacement force along the slit 52 (if the needle 60 passes through the slit 52) to dilate the slit 52 while the system 5 is in storage prior to use. This larger displacement force has the potential to induce a set in the elastomeric sealing member 44 over the shelf life of the system 5, which can reduce the sealing force of the slit 52 or perforation at the site of the indwelling needle 60. When a needle 60 is employed with catheters of greater than 20 gauge, the diameter needle 60 can be narrowed along at least one axis along the proximal region 63 of the needle (shown indwelling within the elastomeric sealing member 44 adjacent the needle hub 75 in FIG. 1). The outer diameter within this proximal region 63 can be reduced to a diameter equivalent to that of needles conventionally employed with 20 gauge catheters. If preferred, the diameter can be reduced along only one axis and elongated in another to provide for adequate internal diameter of the lumen 67 for blood flow during the blood flashback process. The region 63 can be provided as an ellipse (not shown) and then inserted so the longer axis is aligned with the slit 52. Alignment guides can be used if desired during assembly to align the slit and the long axis of the ellipse. Also during assembly a steel trocar with a blunt rounded surface can be provided within the needle 60 to prevent damage by the needle tip during insertion into the slit 52 during assembly.

Figure 3:
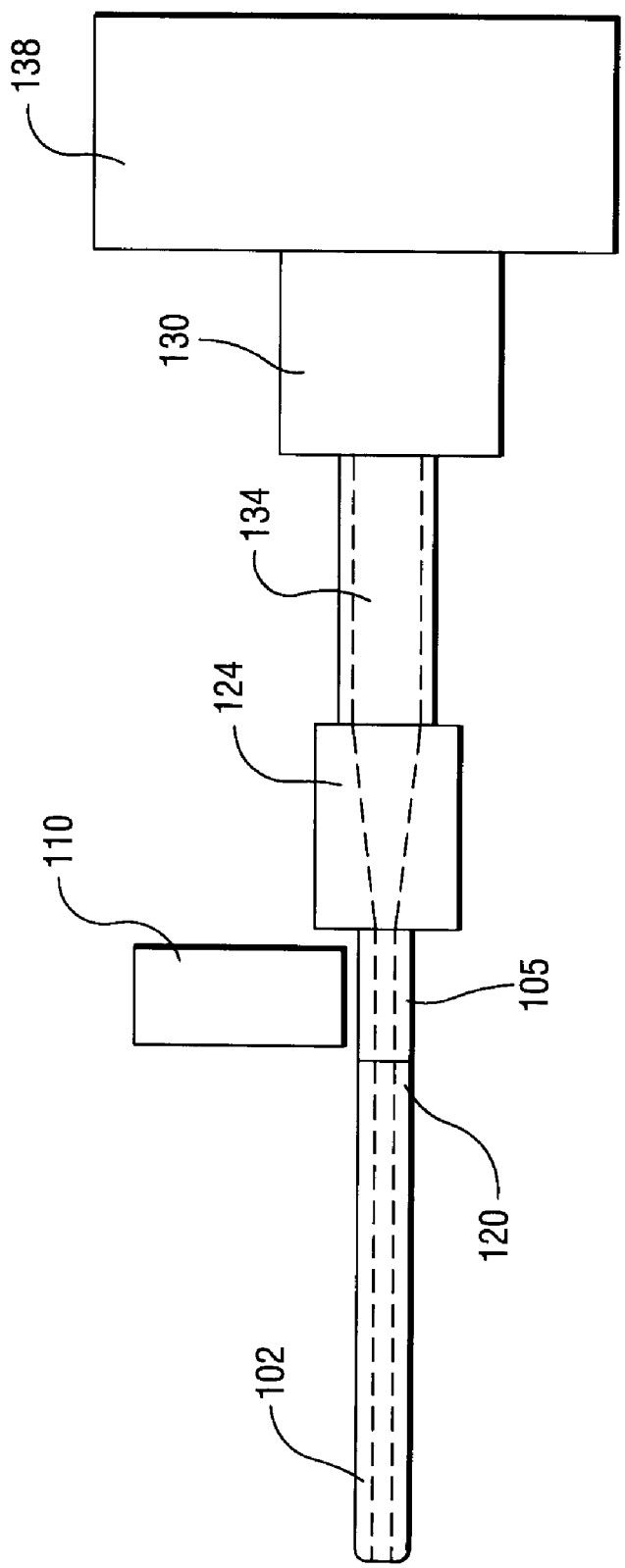
FIG. 3 is a schematic of an ex vivo blood-testing catheter according to the present invention.

FIG. 3 shows a schematic diagram of another type of the new safety access system, for blood testing. An ex-vivo blood-testing catheter 100 includes a tubular catheter body 102, a blood testing site 105 for interfacing with a sensor 110 for ex-vivo testing of the blood from the catheter body 102. The test site 105 is preferably provided adjacent the proximal end 120 of the catheter body 102. Although not shown a blood sampling port as for receiving a micro-sampler as shown in FIG. 22 of my U.S. Pat. No. 5,562,639 (the disclosure of which is incorporated by reference as if completely disclosed herein) or other blood sampling device can also be provided adjacent the hub 124. The advantage of providing a test site or blood sampling port adjacent the proximal end of the catheter body 102, especially when it is used with a short catheter, is that only very small volume of blood need be displaced into system to provide undiluted blood at the test site. Conventionally the withdrawal of a volume of 5 times the deadspace has been considered sufficient to achieve an undiluted blood sample at a site for test. This is discussed in my U.S. Pat. No. 4,838,855, (the disclosure of which is incorporated by reference as if completely disclosed herein). However, because, in the instant invention the test chamber 105 is positioned adjacent the proximal end 120 of a very small bore smooth catheter body 102, the flow will be turbulent due the small diameter of the lumen and the volume required will be very low since large variations in tubular dimensions are not present along the withdrawal pathway distal the test site 105 and the amount of deadspace is very low for example with a 20 g, 1 inch catheter. When the catheter is a small one inch peripheral catheter of 20 gauge, only one cc of blood or less need be withdrawn into the catheter to obtain undiluted blood at the test site 105. Such a blood testing catheter is ideal for making intermittent measurements of blood parameters such as oxygen saturation or glucose since it can be connected proximally to a very low volume blood withdrawal apparatus or pump 130 which is very easily mounted with the patient. This can include for example a patient mounted covered tuberculin syringe or a small rolling or sliding peristaltic pump 130 mounted on length of tubing adjacent the catheter hub 124. These small pumps allow for very small reciprocating volumes within the catheter body 102 to reciprocate blood into the sample test site 105 for testing (or blood removal if a port is mounted to the catheter at this location). A capacitance tubing 134 such as a short segment of tubing of slightly greater diameter than convention catheter pigtail tubing can be provided intermediate the pump and the test site so that blood does not enter the peristaltic or other pump. A fluid source 138 can be provided to provide additional flush of the system after the process has been completed. This system eliminates the need for multiple needle sticks for blood testing or sampling.

Figure 4:
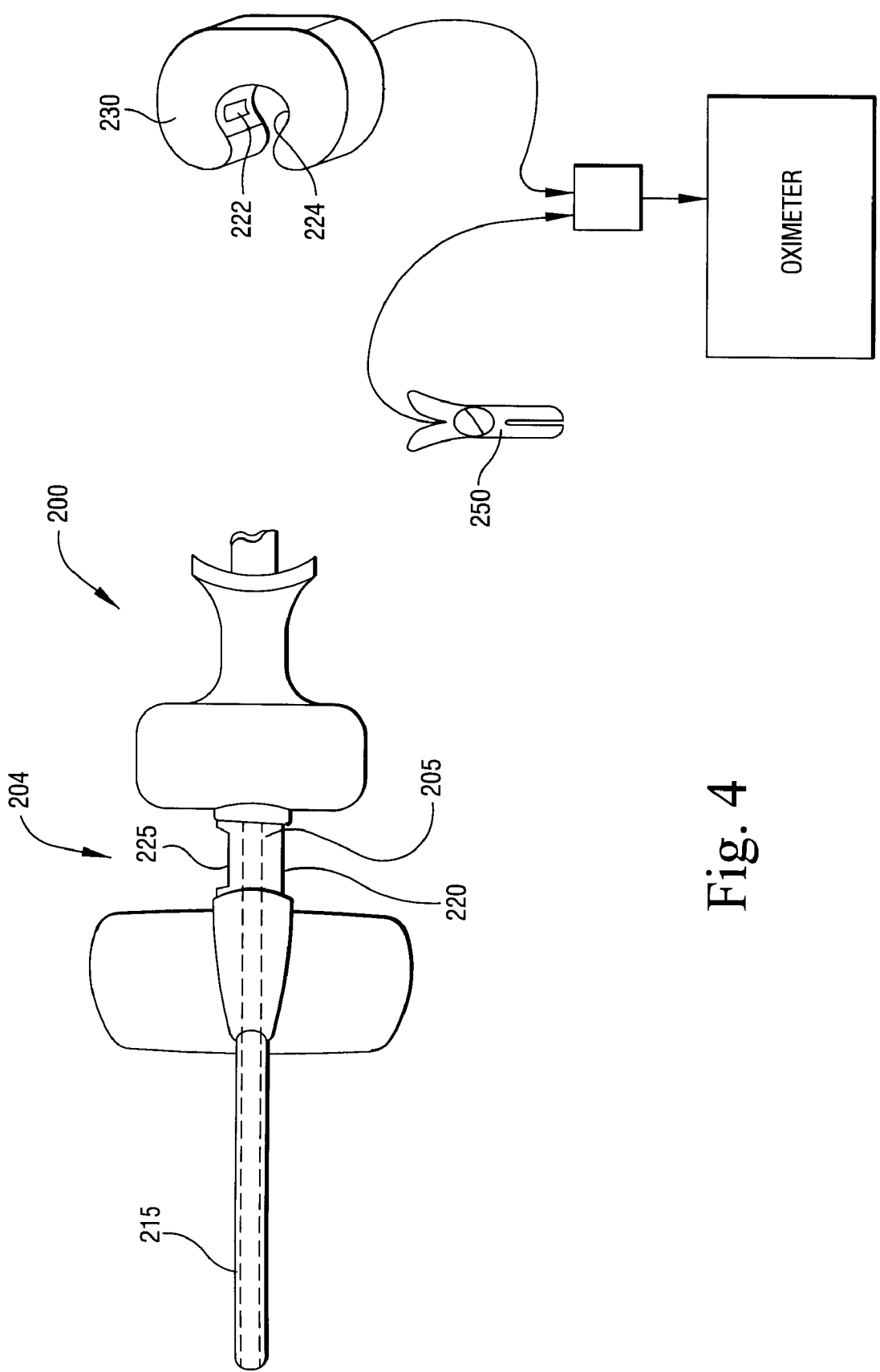
FIG. 4 is a top and schematic view of ex-vivo oximetry blood testing catheter system according to the present invention.

FIG. 4 shows one preferred embodiment of the safety catheter 200 portrayed in FIG. 3. This catheter provides for the determination of oxygen saturation in situations of the low perfusion or cold (commonly present during major surgical procedures) wherein the conventional pulse oximeter provides an inadequate reading. With this embodiment the test site 204 is comprised of a short length of flexible tubing 205 mounted to the proximal end of the catheter 215. A pair of opposing windows 220 for receiving a probe 230 sized to be received into the windows 220 which includes conventional a light emitting diode 222 and opposing light sensor 224 which fit into the windows 220 with the probe 230. The tube 205 can be flattened in one dimension to provided at least one thinned and flattened face 225 perpendicular to the light emitting diode 222. The flattened face 225 of the wall of the tube 205 adjacent the window 220 is preferably 1 mm or less and is comprised of elastic silicone of a Durometer of less 30 and which will pulsate with each pulse in the vascular system. In operation, the catheter is inserted into an artery, and the LED and receiver is fit into the windows, when blood is withdrawn into the tube the blood will pulsate providing a direct reading of oxygen saturation for the pulse oximeter. The pulse oximeter can be connected with a conventional probe 250 through a conventional or other switching mechanism 260. In a similar way miniaturized blood glucose sensors, as are known in the art, may be mounted adjacent the sample site so that a blood glucose reading can be obtained whenever desired by simply reciprocating blood into the sample site.

Figure 5:
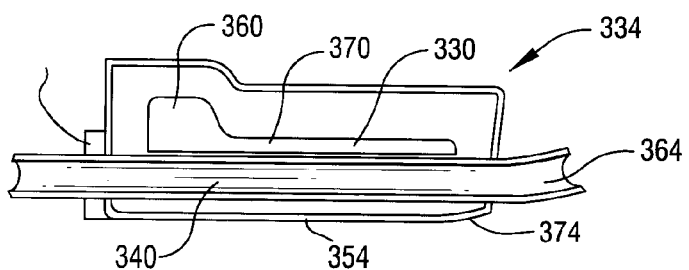
FIG. 5 is a side view a peristaltic pump system according to the present invention.
Figure 6:
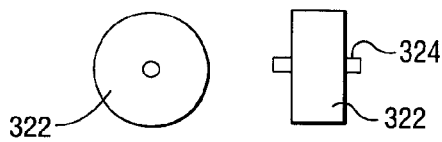
FIG. 6 is a side and front view of the wheel of the pump system of FIG. 5.
Figure 7:
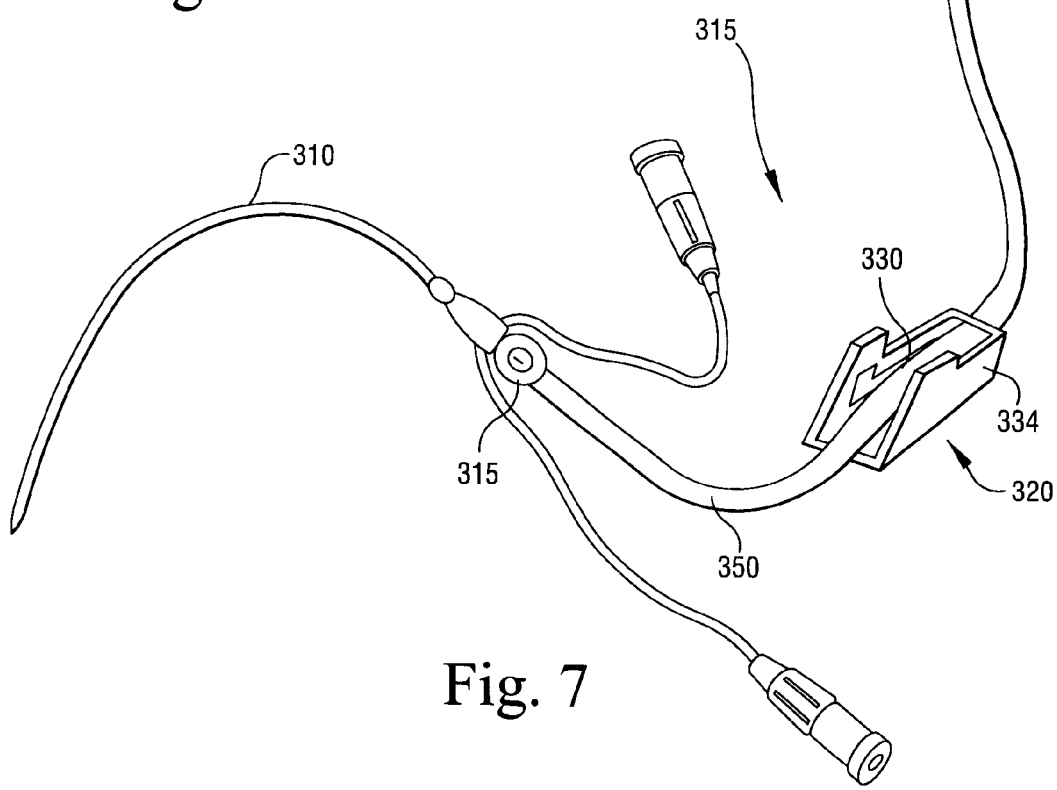
FIG. 7 is an orthogonal view of a closed blood sampling system according to the present invention.

FIGS. 5, 6 and 7 show a closed low volume, catheter and pump system 300 for the enclosed reciprocation of blood into the multi-lumen catheter body 310 and luer receiving sampling site 315 which can be used with a safety catheter as described supra or with as a multi-lumen catheter (as shown). A small pump 320 comprises a rolling wheel 322 mounted having opposing axles 324 which fit into opposing parallel tracks 330 on a tram 334 in which the wheel axles 324 slide or roll. The tracks 330 are mounted along a short segment of flexible tubing 340 adjacent a capacitance tubing segment 350. At least one stop 342 provided to prevent migration of the tram 334 along the tubing 350. The tram includes a floor 354 against which the flexible tubing 340 is compressed when the wheel 322 is advanced along the tram 334. The track 330 provides a distal enlargement in the distal upper track 360 adjacent the capacitance tubing 350 to allow the axles 324 and wheel 322 to deflect upwardly to release the compression of the segment away from the floor 354 when the wheel is in the most distal position so that the flow pathway 364 through the tubing is open when the wheel is in the most distal position.

A mid portion of the tram 370 is provided wherein the tracks remain parallel to the floor so that progressive increase in compression does not occur within this region allowing ease of rolling and associated displacement of blood into the catheter body 310. At its most proximal extent 374, the floor 354 angles slightly toward the tracks 330 to induce an increase in compression of the tubing and frictional force resulting in a fixed position of the wheel 322 when it is advanced to the most proximal position. The tubing segment 340 is preferably comprised of a flexible and resilient polymer such a silicone so that it is easily compressed and yet rebounds to its original shape upon movement of the wheel back to the distal position. When the lumen is the most proximal lumen of a multi-lumen catheter. The segment preferably includes a lumen of about 2.5–4 mm in diameter and is preferably about 3.5 to 6 cm in length. The rolling compression of this segment displaces a volume into the catheter body and sample or test site sufficient to displace all resident fluid from the test site so that undiluted blood collection or blood measurements can be made.

In operation the wheel is in its most proximal position with the tubing in an uncompressed and open state. When a sample or test is desired the wheel is retracted along the segment progressively compressing the segment against the floor. At its most proximal extent the compression is increased by the distal upward slope of the floor so that the wheel is fixed with the tube closed and compressed when the wheel is in its most proximal position. The retraction of the wheel and sequential compression of the segment effectively withdraws sufficient blood into the catheter body and test site that undiluted blood is present at the test site for sampling or test. The test is then made or sample collected. The wheel is then advanced along the segment to push the blood back through the catheter body into the patient's vasculature. When the wheel is fully advanced the wheel enters the enlarged segment of the track and deflects upward so that the segment is released and no longer compressed. Additional fluid can then be flushed through the system from the fluid source.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A self sealing catheter system for connection with a female threaded housing of a luer lock connector of a fluid administration system and for providing self sealing fluid connection between a patient's vascular system and a male luer contained within said housing, the system comprising:
    a) a catheter defining at least one flow channel,
    b) a hollow needle projecting though said flow channel the needle having a needle hub and a sharp tip,
    c) a needle cover mounted adjacent said needle hub for covering said sharp tip when said needle is removed from the catheter,
    d) a luer receiving valve sized to be received within said female threaded housing, said valve being mounted with said system in fluid connection with said flow channel.

2. The system of claim 1 wherein needle projects through said valve.

3. The system of claim 1 wherein said valve comprises an elastomeric septum mounted with a rigid septum housing.

4. The system of claim 3 wherein said septum includes a slit for engaging said male luer.

5. The system of claim 4 wherein said slit is sized for receiving said male luer so that said male luer at least partially penetrates into said septum at least partially through said slit when said male luer is advanced against said septum.

6. The system of claim 1 wherein said catheter includes a proximal hub, said valve being connected with said catheter hub.

7. The system of claim 6 wherein said valve is integral with said catheter hub.

8. The system of claim 6 wherein said valve comprises said catheter hub.

9. The system of claim 2 including a needle retractor, the needle being retracted by said retractor through said valve so that said tip is covered by said needle cover.

10. The system of claim 2 wherein said needle cover is connected with said luer-receiving valve so that when said needle is retracted from said catheter through said valve said needle tip is covered by said cover.

11. The system of claim 2 wherein said needle cover is connected with said luer receiving valve such that said cover is detachable from said luer receiving valve after said needle has been retracted from said valve.

12. The system of claim 1 wherein said needle cover and said needle and said luer receiving valve are mounted together so that said cover and luer receiving valve are automatically disconnected when said needle is retracted from said valve.

13. The system of claim 1 wherein said needle cover is a receptacle.

14. The system of claim 1 wherein said system includes at least one connecting member connecting said needle cover with said luer receiving valve.

15. The system of claim 14 wherein said at least one connecting member comprises said needle.

16. The system of claim 15 wherein said needle projects from said needle hub through said luer receiving valve and through said catheter.

17. The system of claim 11 wherein said needle cover and luer receiving valve are positioned such that, when said needle is retracted and disconnected from said luer receiving valve, said needle cover is thereby automatically disconnected from said luer receiving valve.

18. The system of claim 10 wherein said luer receiving valve automatically seals the flow channel of said catheter upon retraction of said needle from said valve.

19. The system of claim 10 wherein said cover is connected with said luer receiving valve such that said needle cover is detachable from said luer receiving valve.

20. The system of claim 12 wherein said needle hub is mounted within said cover, said needle projecting from said needle hub through said luer receiving valve and through said catheter.

21. The system of claim 13 wherein said needle hub is mounted within said receptacle.

22. The system of claim 10 wherein said luer receiving valve includes a proximal portion, said needle cover being detachably mounted with the proximal portion.

23. The system of claim 3 wherein said septum defines a proximal face for engaging a male luer and said septum housing defines a proximal end, said face being positioned adjacent said proximal end so that, prior to engaging said male luer, said face can be readily swabbed with antiseptic.

24. The system of claim 3 wherein said septum defines a proximal face for engaging a male luer and said septum housing defines a proximal end, said face being positioned adjacent said proximal end said needle cover being mounted adjacent said face.

25. The system of claim 3 wherein needle projects through said valve.

26. The system of claim 24 wherein said needle cover is a receptacle connected with said luer-receiving valve adjacent said face so that said needle can be retracted out of said catheter, through said valve and into said receptacle.

27. The system of claim 26 wherein said receptacle is connected with said luer receiving valve such that said receptacle is detachable from said luer receiving valve after said needle has been retracted into said receptacle.

28. The system of claim 3 wherein said septum defines a proximal face for engaging a male luer, the needle cover being mounted adjacent said face, and wherein said housing defines a proximal end, said face being positioned adjacent said proximal end so that said face can be readily swabbed with antiseptic after the needle has been retracted from the luer receiving valve and the needle cover has been displaced away from said face to expose said face.

29. The system of claim 1 wherein said needle defines an external diameter, and said catheter defines a distal portion, said external diameter being smaller adjacent said septum than adjacent said distal portion.

30. The system of claim 1 wherein said system includes flexible conduit intermediate said catheter and said valve to reduce at least one of the longitudinal and rotational forces transmitted to the catheter in associated with the receipt of said valve into said female threaded housing.

31. The system of claim 1 wherein said valve includes a septum having a perforation, said needle extending through said perforation, said system further including at least one elastic, substantially annular member projecting about said septum for biasing said perforation into a tightly sealed position after said needle has been withdrawn from said septum.

32. The system of claim 31 wherein said elastic member is mounted adjacent said septum.

33. The system of claim 31 wherein said elastic member is integral with said septum.

34. The system of claim 33 wherein said elastic member is an annular projection of said septum, said annular projection applying a compressive force to at least a portion of said perforation to enhance the closure of said perforation when said needle has been withdraw from said perforation.

35. The system of claim 1 further including an integral extension tube mounted in fluid connection with said catheter, said extension tube defining a proximal end, said luer receiving valve being positioned at said proximal end of said extension tube remote from the catheter hub.

36. A self sealing catheter system for connection with a female threaded housing of a luer lock connector of a fluid administration system and for providing self sealing fluid connection between a patient's vascular system and a male luer contained within said housing, the system comprising:
 a) a catheter defining at least one flow channel,
 b) a hollow needle projecting though said flow channel the needle having a needle hub, said needle having a sharp tip,
 c) a needle tip cover device mounted adjacent said needle hub for receiving and covering said needle tip when said needle is removed from said catheter,
 d) a luer receiving valve sized to be received within said female threaded housing said valve being mounted in fluid connection with said flow channel said valve including a septum defining a proximal face for engaging a male luer and said septum housing defining a proximal end, said face being positioned adjacent said proximal end, the luer receiving valve providing a self sealing, swappable, connection terminal for fluid connection between said male luer and said vascular system through said flow channel after said catheter has been inserted into said vascular system and said needle has been withdrawn from said flow channel.

37. The system of claim 36 wherein needle projects through said valve.

38. The system of claim 37 wherein said face includes a slit for first receiving said needle and subsequently receiving said male luer after said needle has been withdrawn from said septum.

39. The system of claim 36 wherein said needle tip cover is detachably mounted adjacent said luer receiving valve such that when said needle has been retracted and covered by said cover, said needle cover can be disconnected from said luer receiving valve so that said face is exposed for engaging with said male luer.

40. The system of claim 39 wherein said luer receiving valve includes a proximal portion, said cover being detachably mounted with the proximal portion.

41. The system of claim 40 wherein said needle cover is a receptacle detachably positioned adjacent said proximal end.

42. The system of claim 36 wherein said needle hub is mounted proximal said face, said hollow needle projecting from said hub, through said septum, through said flow channel, to said sharp tip so that said needle fluid connection between said hub and said vascular system so that blood can flow from said vascular system into said hub proximal said face to provide an indication of penetration of the needle into said vascular system, said hub being displaceable away for said face after said blood has entered said hub, said elastomeric septum providing automatic sealing to prevent additional blood from flowing from said vascular system proximal said face after said needle has been retracted out of said valve, said proximal portion being received into said threaded housing to provide closed fluid connection with said fluid delivery system after said needle has been withdrawn from the septum.

43. The system of claim 36 wherein said needle hub is mounted adjacent said face.

44. The system of claim 36 wherein said needle defines an external diameter, and said catheter defines a distal portion, said external diameter being smaller adjacent said septum than adjacent said distal portion.

45. The system of claim 36 wherein said system includes flexible conduit intermediate said catheter and said valve to reduce at least one of the longitudinal and rotational forces transmitted to the catheter in associated with the receipt of said valve into said female threaded housing.

46. The system of claim 36 wherein said valve defines a fluid chamber distal to said septum, said septum being configured such that substantial negative pressure is mitigated within said fluid chamber when male luer is disconnected from fluid connection with said catheter through said valve.

47. The system of claim 36 wherein said valve defines a fluid chamber distal to said septum, said septum being configurede such that substantial negative pressure is not induced within said fluid chamber when male luer is disconnected from fluid connection with said catheter through said valve.

48. A self sealing catheter system for connection with a female threaded housing of a luer lock connector of a fluid administration system and for providing self sealing fluid connection between a patient's vascular system and a male luer contained within said housing, the system comprising:

a) a catheter defining at least one flow channel, b) a hollow needle projecting though said flow channel the needle having a needle hub the needle having a sharp tip, c) a luer receiving valve sized to be received within said female threaded housing said valve being mounted in fluid connection with said flow channel, d) a needle cover mounted adjacent said needle hub, e) a needle retractor for retracting said needle from said flow channel into a position wherein said cover covers said needle tip after said catheter has been inserted said vascular system.

49. The catheter system of claim 48 wherein said needle cover is a needle receptacle.

50. The system of claim 48 wherein said needle defines an external diameter, and said catheter defines a distal portion, said external diameter being smaller adjacent said septum than adjacent said distal portion.

51. The system of claim 48 wherein said system includes flexible conduit intermediate said catheter and said valve to reduce at least one of the longitudinal and rotational forces transmitted to the catheter in associated with the receipt of said valve into said female threaded housing.

52. The system of claim 48 further including an integral extension tube mounted in fluid connection with said catheter, said extension tube defining a proximal end, said luer receiving valve being positioned at said proximal end of said extension tube remote from the catheter hub.

* * * * *

UNITED STATES PATENT AND TRADEMARK OFFICE
CERTIFICATE OF CORRECTION

PATENT NO. : 6,740,063 B2
DATED : May 25, 2004
INVENTOR(S) : Lynn, Lawrence A.

It is certified that error appears in the above-identified patent and that said Letters Patent is hereby corrected as shown below:

Column 10,
Line 57, replace "swappable" with -- swabbable --

Signed and Sealed this

Second Day of August, 2005

JON W. DUDAS
*Director of the United States Patent and Trademark Office*